US00PP34512P2

(12) United States Plant Patent
Hansen

(10) Patent No.: US PP34,512 P2
(45) Date of Patent: Aug. 16, 2022

(54) *MONARDA* PLANT NAMED 'ELECTRIC NEON PURPLE'

(50) Latin Name: ***Monarda* hybrid**
Varietal Denomination: 'Electric Neon Purple'

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/803,302

(22) Filed: Apr. 28, 2022

(51) Int. Cl.
*A01H 5/02* (2018.01)
*A01H 6/14* (2018.01)

(52) U.S. Cl.
USPC ..... Plt./455

(58) Field of Classification Search
USPC ..... Plt./263.1, 455
See application file for complete search history.

*Primary Examiner* — Karen M Redden

(57) ABSTRACT

The new and distinct cultivar of ornamental cultivar of hybrid ornamental Bee Balm plant named *Monarda* 'Electric Neon Purple' with lanceolate, dark-green, moderately-glossy, powdery mildew-tolerant foliage and flower heads of bright fuchsia-purple flowers for about five weeks. The plant habit is compact and winter-hardy, useful in the landscape as a specimen, en masse, or as a containerized plant.

1 Drawing Sheet

Botanical designation and cultivar denomination:
Botanical classification: *Monarda* hybrid.
Variety denomination: 'Electric Neon Purple'.

STATEMENT REGARDING PRIOR DISCLOSURES UNDER 37 CFR 1.77(B)(6)

The first public disclosure of the claimed plant, in the form of a sale, was made by Walters Gardens, Inc. on May 3, 2021 in a sale to Chrissy's Greenhouse, North Coast Perennials and Sunbeam Gardens. Prior to that, on Feb. 1, 2021 the claimed plant was displayed with a non-enabling photograph and brief description in a website operated by Walters Gardens, Inc., and on May 21, 2021 as a non-enabling photograph and brief description in the "Walters Gardens 2021-2022 Catalog" by Walters Gardens, Inc., who obtained the plant and all information relating thereto, from the inventor. No plants of *Monarda* 'Electric Neon Purple' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Electric Neon Purple', and hereinafter also referred to solely by the cultivar 'Electric Neon Purple' or the "new plant." *Monarda* 'Electric Neon Purple' was the result of a controlled pollination in the summer on Jun. 19, 2015, in the research area at a wholesale perennial nursery in Zeeland, Mich., USA. The female parent is 'Bubblegum Blast' U.S. Plant Pat. No. 27,497 and the specific male parent is a proprietary, unnamed, unreleased hybrid known only as "red pringlei sdlg" (not patented). The new plant was separated out for further evaluation in the summer of 2017 in the full sun trial gardens of the same nursery and assigned the breeder code 15-5-1. The new plant is the result of a planned breeding program of the inventor to produce new colors of flowers with superior mildew resistance, and improved compact habit. The new plant has been asexually propagated since 2017 by division and by basal stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Electric Neon Purple' is unique from its parents and all other Bee Balm plants known to the inventor. The nearest comparison cultivars known to the inventor are: 'Pardon My Lavender' U.S. Plant Pat. No. 28,770, 'Electric Neon Pink' U.S. Plant Pat. No. 30,347, 'Pardon My Lavender II' U.S. Plant Pat. No. 34,131, and 'Lilac Lollipop' U.S. Plant Pat. No. 27,571.

'Pardon My Lavender' has less vigor and powdery mildew resistance and lavender-pink flowers and the habit is slightly smaller and compact. 'Electric Neon Pink' has similar size and habit, but the flowers are intense neon-pink color with darker purple spots on the lower labium. 'Pardon My Lavender II' has a smaller habit and the flowers are lavender-purple. 'Lilac Lollipop' is comparable in habit, but the flowers are lavender-lilac colored.

The female parent differs with a hot pink flower color. The male parent has a taller habit and the flowers are more reddish and the leaves are smaller and narrower with red floral bracts and tends to develop a reddish fall color, and is less winter hardy and weaker-stemmed and more taxed in habit.

*Monarda* 'Electric Neon Purple' is distinct from all Bee Balm plants known to the inventor. The following are traits of the new plant that in combination distinguish it from all other Bee Balm known to the inventor:

1. Deep-green, moderately-glossy, powdery mildew-tolerant foliage;

2. Medium, dense, clumping, upright mound that is winter-hardy habit;
3. Flowers are bright fuchsia-purple and remain effective for about a five-week-long period beginning late spring;
4. Bracts subtending inflorescences with deep reddish and wine coloration;
5. Flowering in dense verticils.

BRIEF DESCRIPTION OF THE DRAWINGS

The photographs of the new plant demonstrate the unique traits of *Monarda* 'Electric Neon Purple' and the overall appearance of the plant at three-years-old in the full sun display garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
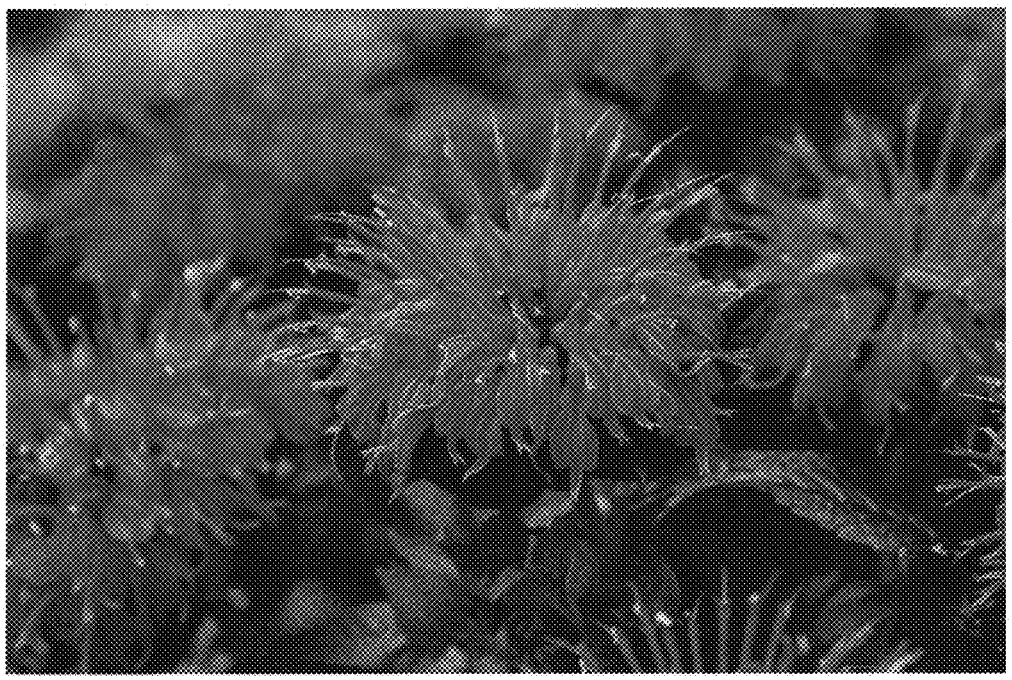
FIG. 1 shows a close-up of the flower of the new plant.
Figure 2:
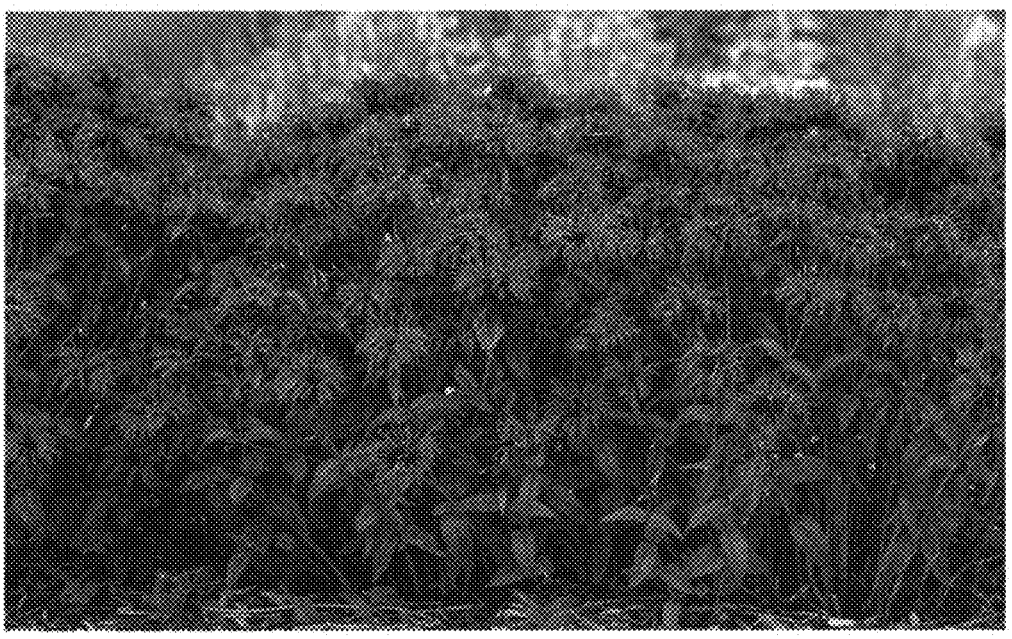
FIG. 2 shows the habit of the new plant in full flower.

The following descriptions and color references are based on the 2015 edition of The Royal Horticultural Society Colour Chart except where common dictionary terms are used. *Monarda* 'Electric Neon Purple' has not been observed under all possible environments. The phenotype may vary slightly with different growing environments such as temperature, light, fertility, soil pH, moisture and maturity levels, but without any change in the genotype. The following observations and size descriptions are based on two-year-old plants grown in a trial garden and a partially shaded greenhouse at a nursery in Zeeland, Mich. with supplemental fertilizer and water as needed.

Botanical classification: *Monarda* hybrid;

Parentage: The female (seed) parent is 'Bubblegum Blast', an unreleased proprietary hybrid; the male (pollen) parent is known only as "red pringlei sdlg";

Plant habit: Hardy herbaceous perennial, dense, upright mound, producing multiple stems spreading by short rhizomes near the base of the stems; foliage up to 40.0 cm tall, flowering to 60 cm tall and 76 cm wide; flowering begins early summer in Michigan and continuing for about 5 weeks;

Propagation: Stem cuttings;

Time to produce finished crop in 3.8-liter pots: About 7 to 9 weeks; moderate rate of growth;

Root: Fine, fibrous and freely branching; color creamy white to tan depending on soil type;

Leaves: Simple; lanceolate; opposite; margin serrated and micro-ciliolate; puberulent above and below; moderately lustrous adaxial, abaxial matte in maturity to slightly lustrous when expanding; narrowly acute apex; cordate to rounded base; to about 7.5 cm long and 3.8 cm wide, average about 6.0 cm long and 2.6 cm wide near base of leaf;

Leaf color: Young expanding leaves adaxial between RHS 143A and RHS 146B with light overtone of nearest RHS 187A, abaxial nearest RHS 146B without obvious anthocyanin pigmentation; older leaves adaxial nearest RHS 139A with portions high in anthocyanins nearest RHS 187A, abaxial nearest RHS 137B with portions high in anthocyanins nearest RHS 187B; Foliage fragrance: pleasant lemony-herbal;

Veins: Pinnate; glabrous and slightly sunken adaxial, micro-pubescent and costate abaxial;

Vein color: Adaxial midrib nearest RHS 146C and lateral pinnate veins and secondary veins between RHS 145A and RHS 146D; abaxial midrib nearest RHS 146D with frequent moderate to weak anthocyanin blush of nearest RHS 187B and with lateral pinnate veins and secondary veins nearest RHS 146B without obvious anthocyanin blush;

Petiole: Micro-puberulent and slightly concaved adaxial; puberulent and convex abaxial; ciliolate margin; to about 6.0 mm long and 2.0 mm across at base;

Petiole color: Adaxial nearest RHS N186C, abaxial nearest RHS 146D with a slight to strong blush of nearest RHS N186C in high light exposure;

Stems: Quadrangular; puberulent; about 5.0 mm across at base; about 50 per plant; naturally branched at upper and lower nodes; average 4.2 cm between nodes greater distally; 9 to 12 nodes per stern; average length about 52 cm;

Stem color: Nearest RHS 146C with heavy anthocyanin expression in high light nearest RHS 187A; nodes same color as surrounding stem;

Flowers: Single; bilabiate flowers arranged in mostly terminal verticils forming globular head about 84.0 mm across and 39.0 mm tall, opening from the center and progressing outwardly and down; attitude outwardly to upwardly; individual flowers to about 38.0 mm long to exserted stigma, 20.0 mm tall and about 5.5 mm across; individual flowers persisting about 5 days in Michigan; numerous, about 200 flowers per terminal head, fewer per axillary head; 105 inflorescences with open flowers at one time;

Flower fragrance: Sweetly lemony;

Buds one to two days prior to opening: Narrowly oblanceolate, arcuate downward; about 20.0 mm long and 2.0 mm across and 6.0 mm tall;

Bud color: Basal 3.0 mm between RHS157D and RHS NN155B, ventral and dorsal middle portion nearest RHS N80A, distal ventral and dorsal region nearest RHS 83A;

Petals: Bilabiate; arcuate downward; basal 20.0 mm fused into tube; split in two in the distal 16.0 mm; abaxial glandular to puberulent, adaxial glabrous in free portion and micro-puberulent in corolla tube; self-cleaning;

Upper labium: Rolled or folded in free portion, about 13.0 mm long from fusion to emarginate apex with notch about 0.5 mm deep; 2.0 mm tall, 2.0 mm across at base, about 4.0 mm across in middle when flattened;

Lower labium: About 16.0 mm long from fusion to apex, apex comprising three lobes including two side lobes about 1.0 mm long and 2.0 mm across with rounded apex, center lobe about 5.0 mm long with emarginate apex in the distal 1.0 mm;

Petal color: Upper labium adaxial surface between RHS N80B and RHS 72B, upper labium abaxial surface between RHS N80A and RHS 72A; lower labium adaxial between RHS N80B and RHS 72B with two lighter longitudinal lines about 1.0 mm wide nearest RHS N75B running on each side of the longitudinal center from fusion point to proximal center lobe, distal apex of center lobe nearest RHS N75C, abaxial surface between RHS N80A and RHS 72A; corolla tube adaxial basal 5.0 mm nearest RHS NN155D and distally between RHS N77D and RHS 77C with veins nearest RHS 76C, abaxial proximal 5.0 mm nearest RHS NN155C and distally between RHS 70A and RHS 72A;

Androecium: Two; adnate inner corolla tube in basal portion;

*Filaments*.—Two; curved downward; adnate the inner corolla tube in the basal 18.0 mm and free in the distal 16.0 mm; about 0.5 mm diameter; color nearest RHS 76C in basal adnate portion and nearest RHS 70B in free portion.

*Anther*.—Oblong elliptic; dorsifixed; longitudinal; two, fused laterally; 2.0 mm long by 1.0 mm wide; dorsal color nearest RHS N79B and ventral suture color nearest RHS N186B.

*Pollen*.—Abundant, elliptic to globose, less than 0.1 mm; color nearest RHS 11B.

Gynoecium: One; superior; about 34.0 mm long;

Pistil: One per flower; protruding about 5.0 mm beyond upper labium when mature;

Style: Cylindrical; glabrous; about 32.0 mm long and about 0.5 mm diameter; arcuate along upper labium; color between RHS 79D and RHS 72B in distal 10.0 mm, transitioning to nearest RHS NN155D in basal 5.0 mm portion;

Stigma: Unevenly bifid in the distal 1.0 mm w79 64D;

Ovary: Conical; about 1.0 mm tall by 0.75 mm diameter; color nearest RHS 145D;

Calyx: Tubular to campanulate; consisting of five fused sepals; about 9.0 mm long and 3.0 mm diameter at apex;

Sepals: Five; acute apex; basal 7.5 mm fused forming calyx tube, free in distal 1.5 mm; margin micro-serrulate; about 9.0 mm long and 1.0 mm across at fusion; glabrous abaxial, glabrous adaxial; persistent;

Sepal color: Adaxial and abaxial basal 1.0 mm nearest RHS 161D, middle adaxial portion nearest RHS 194A with veins nearest RHS N86B, free portion adaxial and abaxial nearest RHS N186B, abaxial middle potion nearest RHS N186C with veins nearest RHS N186B;

Foliar bracts: Typically, one set of five to seven large bracts on the outside per inflorescence, and one set of six smaller bracts in the middle, and one set of about 24 to 30 smaller narrow bracts on the inside directly below each inflorescence; outer bracts lanceolate with acute apex and attenuate sessile base, micro-ciliolate margin, glabrous adaxial, puberulent abaxial, flat to coarsely wavy, matte adaxial and abaxial, lower bract to 45 mm long and 16 mm wide in middle; middle six bracts linear with narrowly acute apex and truncate base, ciliolate margin, glabrous adaxial and micro-puberulent abaxial, to about 20 mm long and 5 mm across near middle; innermost bracts linear, narrowly acute apex and truncate base, ciliolate margin, adaxial and abaxial glabrous, to about 15 mm long and 2.5 mm across at base;

Foliar bract color: Lower bracts adaxial between RHS 187A and RHS N186B distally transitioning to nearest RHS 139A in middle and RHS 145B at base, midrib nearest RHS 186A, color abaxial nearest RHS 138B, midrib nearest RHS 145C with variable blush of nearest RHS 187B; middle six bracts adaxial distal nearest RHS 187A, middle portion nearest RHS 137B with midrib nearest RHS 186A and base nearest RHS 145D, abaxial color nearest 146C in middle with apex strongly blushed with RHS 187A and base nearest RHS 145D; innermost bracts variable, distally adaxial and abaxial nearest RHS 187B and proximally adaxial and abaxial transitioning to nearest RHS 145D at base;

Peduncle: Pubescent, stiff, strong, erect, quadrangular; to about 3.0 mm across and average 52 mm long above last node; about 50 per plant; naturally branched at nodes;

Peduncle color: Variable between RHS 146C in more shaded location and RHS 187A with high light exposure;

Pedicel: About 1.0 mm long and 0.8 mm diameter; color nearest RHS 145B;

Fruit: Single, glabrous, lustrous, ellipsoidal nutlet; about 1.2 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew *Neoerysiphe galeopsidis* (formerly *Erysiphe chicoracearum*) tolerance in side-by-side comparison with other *Monarda*.

I claim:

1. A new and distinct cultivar of hybrid ornamental Bee Balm, *Monarda* plant named 'Electric Neon Purple', as herein described and illustrated.

* * * * *